United States Patent
Cho et al.

(10) Patent No.: US 8,062,227 B2
(45) Date of Patent: Nov. 22, 2011

(54) HEART FAILURE DECOMPENSATION DETERMINATION

(75) Inventors: Yong K. Cho, Maple Grove, MN (US); Shantanu Sarkar, Roseville, MN (US); Douglas A. Hettrick, Andover, MN (US); Robert T. Taepke, II, Coon Rapids, MN (US); Tommy D. Bennett, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 479 days.

(21) Appl. No.: 12/261,389

(22) Filed: Oct. 30, 2008

(65) Prior Publication Data

US 2010/0113888 A1    May 6, 2010

(51) Int. Cl.
*A61B 5/0215* (2006.01)
(52) U.S. Cl. .................. 600/508; 600/485; 600/547
(58) Field of Classification Search .................. None
See application file for complete search history.

(56) References Cited

U.S. PATENT DOCUMENTS

| | | | |
|---|---|---|---|
| 5,368,040 A | 11/1994 | Carney | |
| 5,535,752 A | 7/1996 | Halperin | |
| 5,564,434 A | 10/1996 | Halperin | |
| 6,438,408 B1 | 8/2002 | Mulligan | |
| 6,580,946 B2 | 6/2003 | Struble | |
| 6,599,250 B2 | 7/2003 | Webb | |
| 6,865,419 B2 | 3/2005 | Mulligan | |
| 7,367,951 B2 | 5/2008 | Bennett | |
| 7,404,802 B2 * | 7/2008 | Siejko et al. | 600/528 |
| 7,774,055 B1 * | 8/2010 | Min | 600/547 |
| 2004/0147969 A1 | 7/2004 | Mann et al. | |
| 2005/0027323 A1 | 2/2005 | Mulligan et al. | |
| 2006/0020295 A1 | 1/2006 | Brockway et al. | |
| 2006/0167516 A1 | 7/2006 | Kjellstrom et al. | |
| 2007/0142732 A1 | 6/2007 | Brockway et al. | |
| 2008/0091114 A1 | 4/2008 | Min et al. | |
| 2008/0157980 A1 | 7/2008 | Sachanandani et al. | |
| 2008/0162182 A1 | 7/2008 | Cazares et al. | |

FOREIGN PATENT DOCUMENTS

| | | |
|---|---|---|
| WO | WO 03/037428 A2 | 5/2003 |
| WO | WO 2006/081432 A1 | 8/2006 |
| WO | WO 2008/014078 A2 | 1/2008 |

OTHER PUBLICATIONS (PCT/US2009/059151) PCT Notification of Transmittal of the International Search Report and the Written Opinion of the International Searching Authority, 10 pages.

* cited by examiner

*Primary Examiner* — Kennedy Schaetzle
(74) *Attorney, Agent, or Firm* — Michael C. Soldner

(57) ABSTRACT

Heart failure decompensation is detected by sensing at least one physiological signal. Values of at least two different heart failure variables are derived using one or more physiological signals and a threshold for the first heart failure variable is adjusted in response to the value of the second heart failure variable. The value of the first heart failure variable is compared to first threshold for detecting a heart failure condition.

21 Claims, 10 Drawing Sheets

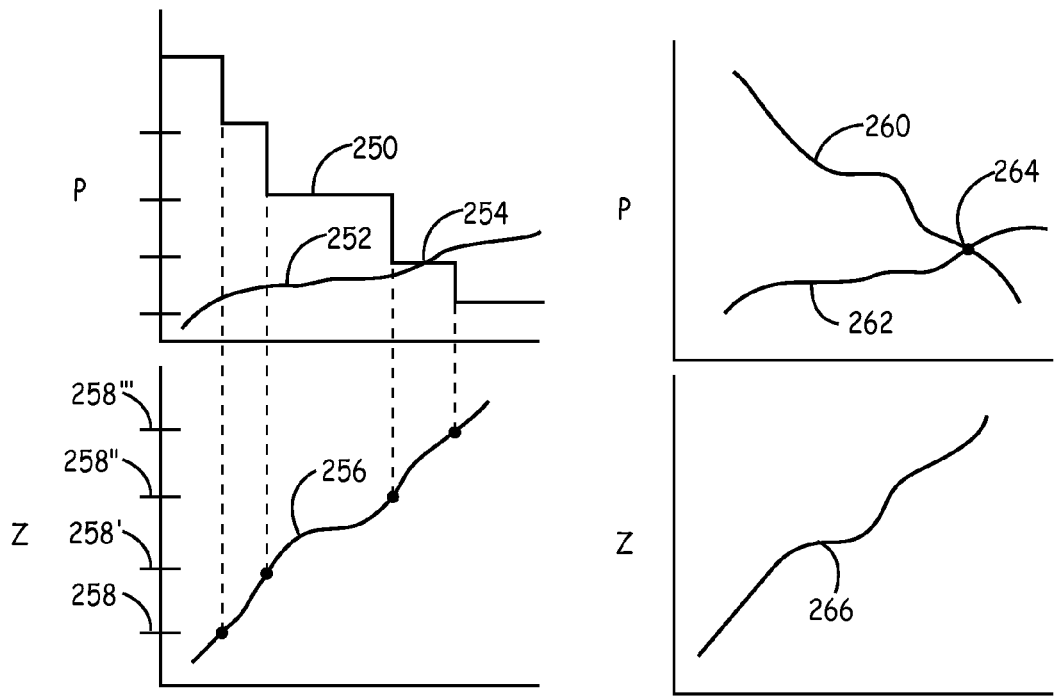
FIG. 4A
FIG. 4B
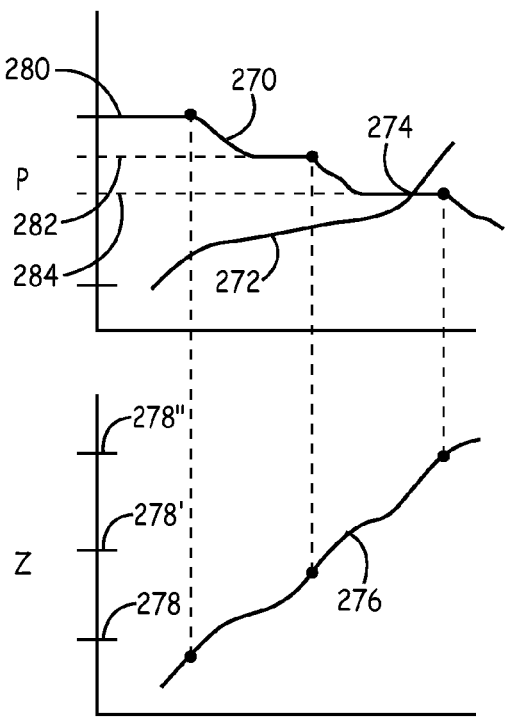
FIG. 4C

400
DETECT TRUTH TABLE

| Pressure (402) | Impedance (404) | Result (406) |
|---|---|---|
| 0 | 0 | No event detected — 412 |
| 0 | 1 | No event detected — 414 |
| 0 | 2 | 418 — WARN |
| 1 | 0 | No event detected — 414 |
| 1 | 1 | DETECT ⎤ |
| 1 | 2 | DETECT ⎦ 416 |
| 2 | 0 | 418 — WARN |
| 2 | 1 | DETECT ⎤ |
| 2 | 2 | DETECT ⎦ 416 |

FIG. 8A

401
RESET TRUTH TABLE

| Pressure (402) | Impedance (404) | Result (406) |
|---|---|---|
| 0 | 0 | RESET ⎤ |
| 0 | 1 | RESET ⎥ 420 |
| 0 | 2 | RESET ⎥ |
| 1 | 0 | RESET ⎦ |
| 1 | 1 | Detect remains valid ⎤ |
| 1 | 2 | Detect remains valid ⎦ 422 |
| 2 | 0 | RESET — 420 |
| 2 | 1 | Detect remains valid ⎤ |
| 2 | 2 | Detect remains valid ⎦ 422 |

HEART FAILURE DECOMPENSATION DETERMINATION

TECHNICAL FIELD

The disclosure relates generally to implantable medical devices and, in particular, to an implantable medical device (IMD) and associated method for detecting or predicting heart failure decompensation.

BACKGROUND

Implantable medical devices are available for monitoring physiological signals for use in diagnosing and managing cardiac disease. For example, implantable hemodynamic monitors can monitor heart rhythm, blood pressure and thoracic fluid status for tracking the status of heart failure patients. In the early stages of heart failure, compensatory mechanisms occur in response to the heart's inability to pump a sufficient amount of blood. One compensatory response is an increase in filling pressure of the heart. The increased filling pressure increases the volume of blood in the heart, allowing the heart to more efficiently eject a larger volume of blood on each heart beat. Increased filling pressure and other compensatory mechanisms can initially occur without overt heart failure symptoms.

The mechanisms that initially compensated for insufficient cardiac output lead to heart failure decompensation as the heart continues to weaken. The weakened heart can no longer pump effectively causing increased filling pressure to lead to chest congestion (thoracic edema) and heart dilation, which further compromises the heart's pumping function, and the patient begins the "vicious cycle" of heart failure which generally leads to hospitalization. By detecting or predicting heart failure decompensation early, even before the patient becomes overtly symptomatic, hospitalization may be avoided through careful therapy management.

BRIEF DESCRIPTION OF THE DRAWINGS

FIGS. 4A, 4B and 4C are diagrams illustrating other methods for setting a variable threshold for use in detecting or predicting heart failure decompensation.

FIG. 8A is a truth table that may be used in setting a warning or detection state, and FIG. 8B is a truth table that may be used in ending a warning or detection state.

DETAILED DESCRIPTION

Figure 1:
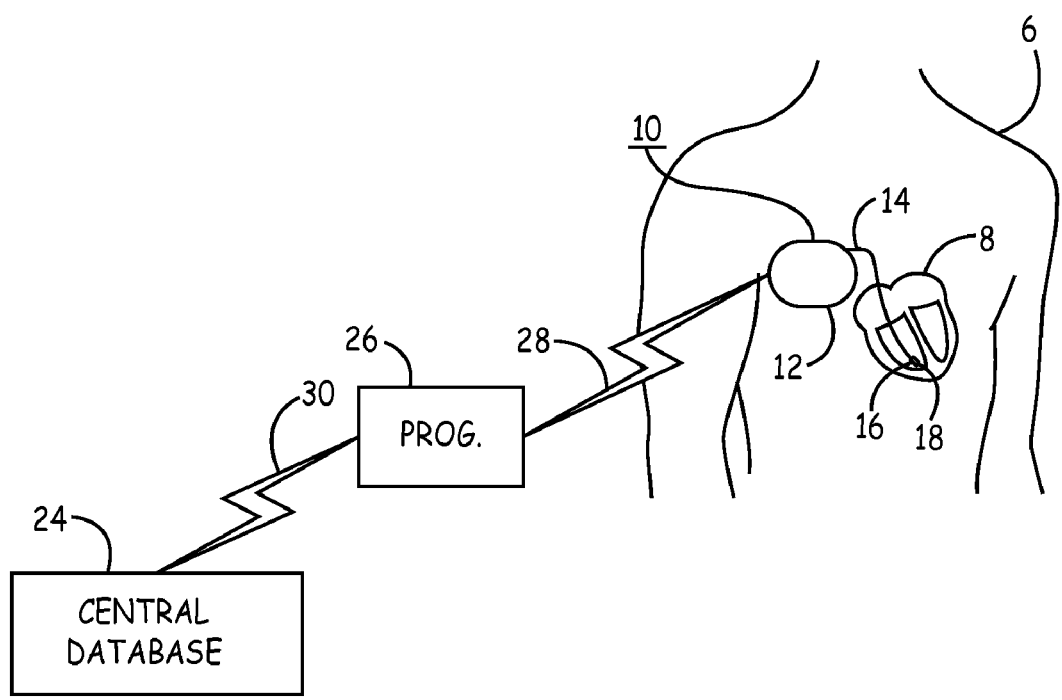
FIG. 1 is a schematic diagram of an implantable medical device (IMD) coupled to a lead positioned within a heart in a patient's body.

In the following description, references are made to illustrative embodiments. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Methods and associated apparatus described herein generally relate to detecting or predicting heart failure decompensation. The term "heart failure decompensation" as used herein generally refers to a worsening state of heart failure, which can potentially lead to hospitalization. Heart failure decompensation can occur gradually over days, weeks or months. The values of monitored physiological variables when a patient becomes overtly symptomatic will likely vary between patients, and physicians will likely have varying preferences regarding the criteria for determining when decompensation is detected and when intervention should be taken. Accordingly, criteria for detecting heart failure compensation may vary between embodiments described herein. Different levels of detection criteria may be used to provide a "warning" when decompensation is likely to be occurring and to provide a "detection" when decompensation is likely to be occurring with even greater certainty based on the values of monitored variables.

Variables used for detecting decompensation are generally referred to herein as "heart failure variables". The term "heart failure variable" as used herein refers to any variable derived from a physiological signal useful in monitoring heart failure status, and in particular heart failure decompensation. A heart failure variable may be the raw data acquired from a sensed physiological signal, a feature of the sensed signal waveform such as a peak, slope, mean, average, or other statistical value. A heart failure variable may alternatively be a value computed from features or statistical values derived from the raw signal. Examples include, but are not limited to, a running average of a cyclic mean value, a cumulative sum of differences between a mean value and a baseline, and so on. Heart failure variables may include hemodynamic variables, e.g., relating to blood pressure. Hemodynamic variables relate to forces involved in the circulation of blood. As such, changes in hemodynamic variables can be good indicators of a change in heart failure status. However other variables not directly relating to blood circulation can be used as indicators of worsening heart failure. For example, increased thoracic fluid level as evidenced by decreased transthoracic impedance is an indication of heart failure decompensation. As such, "heart failure variables" as used herein refers to any variable measured or derived from a sensed physiological signal that correlates to a change in a heart failure condition.

FIG. 1 is a schematic diagram of an implantable medical device (IMD) 10 coupled to a lead 14 positioned within a heart 8 in a patient's body 6. IMD 10 is capable of monitoring at least one physiological signal from which variables useful in monitoring heart failure status can be derived. IMD 10 may or may not be provided with therapy delivery capabilities. IMD 10 may correspond to a variety of implantable medical devices including a cardiac pacemaker, implantable cardioverter defibrillator, implantable hemodynamic monitor, a drug pump, a neurostimulator or the like. Accordingly, IMD 10 may be coupled to additional leads and/or catheters operatively positioned relative to the patient's heart 8 or other body tissues for deploying stimulating/sensing electrodes, other physiological sensors, and/or drug delivery ports. While lead 14 is shown terminated within the right ventricle of the patient's heart, it is recognized that lead 14 may be configured as a transvenous lead that extends into other heart chambers or blood vessels for positioning electrodes and/or physiological sensors in a desired location.

In one embodiment, IMD 10 corresponds to an implantable hemodynamic monitor capable of sensing and recording ECG signals, intracardiac right ventricular pressure signals, and transthoracic impedance signals. IMD 10 may store the sensed signals and further derives heart failure variables from the sensed signals for monitoring the heart failure status of the patient. ECG signals are sensed using one or more electrodes 18 carried by lead 14 or using alternative electrodes (not shown) incorporated on the hermetically-sealed housing 12 of IMD 10. Housing 12 encloses circuitry (not shown in FIG. 1) included in IMD 10 for controlling and performing device functions and processing sensed signals.

An electrode 18 carried by lead 14 is used with the IMD housing 12 for measuring a transthoracic impedance for use in monitoring intrathoracic fluid status. As used herein, "transthoracic" impedance refers to any impedance measurement across a portion of the thorax, including across a portion of the heart, lungs and pulmonary vascular bed. In alternative embodiments, one or more lead-based electrodes and/or one or more subcutaneously placed electrodes, incorporated on IMD housing 12 or carried by a subcutaneously extending lead, may be used to measure a transthoracic impedance across a portion of the thoracic cavity, heart or lungs for use in deriving a variable useful in monitoring heart failure status. Intracardiac impedances may also be used in determining a heart failure variable for monitoring a heart condition. For the purposes of the discussion herein, intracardiac impedance can be considered as one type of transthoracic impedance measurement in that an intracardiac impedance is measured using electrodes within or on the heart to measure impedance across a portion of the heart.

Transthoracic impedance decreases with heart failure decompensation as fluid accumulates in the chest and the heart dilates due to elevated right heart filling pressures and insufficient cardiac ejection. Electrical impedance decreases as the fluid in the chest increases. As such, transthoracic impedance measurements may be used in deriving a heart failure variable useful in detecting heart failure decompensation.

Lead 14 is further provided with a pressure sensor 16. Pressure sensor 16 is used for monitoring pressure within the right ventricle (RV) for use in deriving pressure-related heart failure variable values. The RV pressure signal can be used to estimate pulmonary artery diastolic (ePAD) pressure which increases during heart failure decompensation. While ePAD pressure is one useful variable that can be derived from a RV pressure signal, numerous other pressure-related variables may be useful in detecting heart failure decompensation. Furthermore, pressure signals obtained at other locations in the heart or vasculature may be used for deriving a heart failure variable for detecting or predicting decompensation. Derivation of various pressure-related variables that may be used in monitoring a cardiac condition is generally described in U.S. Pat. No. 6,865,419 (Mulligan) and U.S. Pat. No. 7,367,951 (Bennett), both patents incorporated herein by reference in their entirety.

IMD 10 is capable of bidirectional communication with an external device 26 via telemetry link 28. Device 26 may be embodied as a programmer or home monitor used to program the operating mode and various operational variables of IMD 10 and/or interrogate IMD 10 to retrieve data stored by IMD 10. Stored data may include data related to IMD function determined through automated self-diagnostic tests as well as physiological data acquired by IMD 10 using pressure sensor 16 and electrode(s) 18.

External device 26 is further shown in communication with a central database 24 via communication link 30, which may be a wireless or hardwired link. Programming data and interrogation data may be transmitted via link 30. Central database 24 may be a centralized computer, web-based or other networked database used by a clinician for remote monitoring and management of patient 6. Various methods described herein and executed for determining the heart failure status of a patient using one or more physiological signals sensed by IMD 10 may be implemented in one or more of the IMD system components shown in FIG. 1, namely in the IMD 10, external device 26 and/or central database 24, and may include any combination of hardware, firmware and/or software. External device 26 may be embodied as a clinic-based programmer having full IMD programming and interrogation functionality or a home-based monitor having interrogation and perhaps limited programming functionality and used for remote patient monitoring. It is recognized that other external devices, such as other physiological monitoring devices or other types of programming devices, may be used in conjunction with IMD 10 and incorporate portions of the methods described herein.

Figure 2:
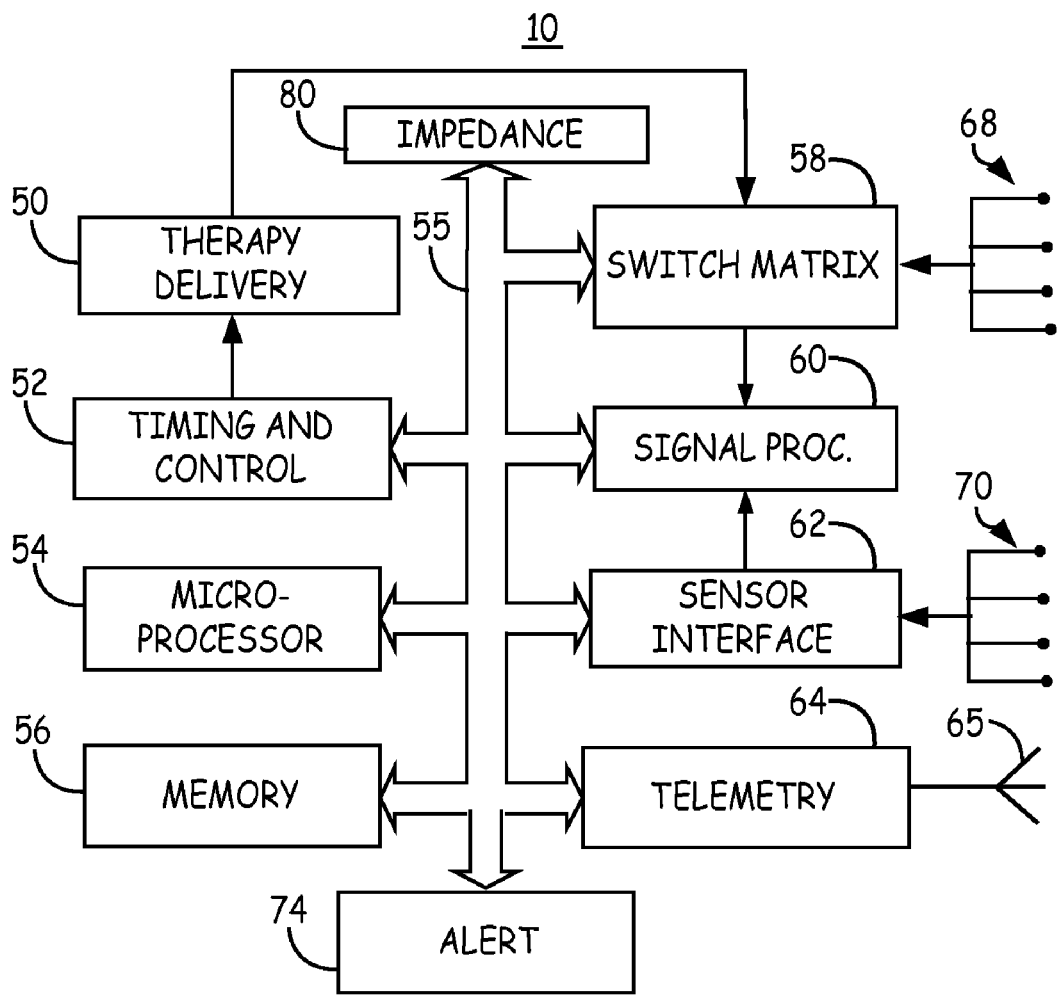
FIG. 2 is a functional block diagram of one embodiment of an IMD.

FIG. 2 is a functional block diagram of one embodiment of IMD 10. IMD 10 generally includes timing and control circuitry 52 and a control unit that may employ microprocessor 54 or a digital state machine for timing sensing and therapy delivery functions (when present) in accordance with a programmed operating mode. Microprocessor 54 and associated memory 56 are coupled to the various components of IMD 10 via a data/address bus 55.

IMD 10 may include therapy delivery module 50 for delivering a therapy in response to determining a need for therapy, e.g., based on sensed physiological signals. Therapy delivery module 50 may provide drug delivery therapies or electrical stimulation therapies, such as cardiac pacing or anti-arrhythmia therapies. Therapies are delivered by module 50 under the control of timing and control circuitry 52. IMD 10 can be implemented as an interrupt-driven device in which case various computations, algorithms, or other device functions are executed upon generation of an interrupt signal.

Therapy delivery module 50 is typically coupled to two or more electrode terminals 68 via an optional switch matrix 58. Switch matrix 58 may be used for selecting which electrodes and corresponding polarities are used for delivering electrical stimulation pulses. Terminals 68 may be coupled to connectors providing electrical connection to electrodes incorporated in IMD housing 12 or other lead-based electrodes, including electrode(s) 18 carried by lead 14 (shown in FIG. 1).

Electrode terminals 68 are also used for receiving cardiac electrical signals through any unipolar or bipolar sensing configuration. Cardiac electrical signals may be monitored for use in diagnosing or managing a patient condition or may be used for determining when a therapy is needed and controlling the timing and delivery of the therapy. When used for sensing, electrode terminals 68 are coupled to signal processing circuitry 60 via switch matrix 58. Signal processor 60 includes sense amplifiers and may include other signal conditioning circuitry and an analog-to-digital converter. Electrical signals may then be used by microprocessor 54 for detecting physiological events, such as detecting and discriminating cardiac arrhythmias.

As discussed above, IMD 10 measures impedance signals for deriving a thoracic fluid status. As such, electrode terminals 68 are used for coupling selected electrodes to impedance measuring module 80 for providing an impedance measurement drive signal along an excitation path. The voltage is then measured across the measuring electrodes allowing the impedance across the measurement path to be computed from the known drive signal and the measured voltage. Impedance measurement methods and associated apparatus are generally disclosed in PCT Publication WO 2008/014078 (Stylos), incorporated herein by reference in its entirety.

IMD 10 is additionally coupled to one or more sensors of physiological signals via sensor terminals 70. Physiological sensors include a pressure sensor 16 as shown in FIG. 1 and may further include accelerometers, flow sensors, blood chemistry sensors, activity sensors, postures sensors, or other physiological sensors used in conjunction with implantable medical devices. Physiological sensors may be carried by leads extending from IMD 10 or incorporated in or on the IMD housing 12.

Signals received at sensor terminals 70 are received by a sensor interface 62 which provides sensor signals to signal processing circuitry 60. Sensor interface 62 receives the sensor signal and may provide initial amplification, filtering, rectification, or other signal conditioning. Sensor signals are used by microprocessor 54 for detecting physiological events or conditions. In particular, signals from pressure sensor 16 are processed by signal processor 60 and/or microprocessor 54 for determining a value of a pressure variable used for evaluating the patient's hemodynamic status.

A heart failure status monitoring algorithm may be stored in memory 56 and executed by microprocessor 54 with input received from electrode terminals 68, sensor terminals 70, processor 60 and impedance measuring module 80. As will be described herein, microprocessor 54 in conjunction with memory 56 operates as a control unit for executing software-implemented algorithms for detecting heart failure decompensation using an impedance variable and a pressure variable derived by processor 60, impedance module 80, and/or by microprocessor 54 using sensed signals. The algorithms may be stored in memory 56 and retrieved therefrom by microprocessor 54 as needed. In alternative embodiments, functionality described herein may be implemented using dedicated hardware and/or firmware.

Heart failure variable data may be stored for use in diagnosing or monitoring the patient or for determining the need for delivering a therapy under control of the operating system. The operating system includes associated memory 56 for storing a variety of programmed-in operating modes and parameter values that are used by microprocessor 54. The memory 56 may also be used for storing data compiled from sensed physiological signals and/or relating to device operating history for telemetry out on receipt of a retrieval or interrogation instruction. Microprocessor 54 may respond to the data by altering a therapy, triggering data storage, enabling other sensors for acquiring physiological data, or triggering alert 74 to generate an alert signal to the patient or a caregiver that a serious condition has been detected that may require medical intervention. Data relating to respiration may be stored in memory 56 for later retrieval.

IMD 10 further includes telemetry circuitry 64 and antenna 65. Programming commands or data are transmitted during uplink or downlink telemetry between IMD telemetry circuitry 64 and external telemetry circuitry included in a programmer or monitoring unit as shown in FIG. 1.

Methods described herein are generally indicated as being executed by the IMD 10 however, as previously mentioned, any of the functionality described herein may be implemented across the components of an IMD system, for example the system shown in FIG. 1, including an IMD, a programmer or home monitor, and a central database for remote patient management.

Figure 3:
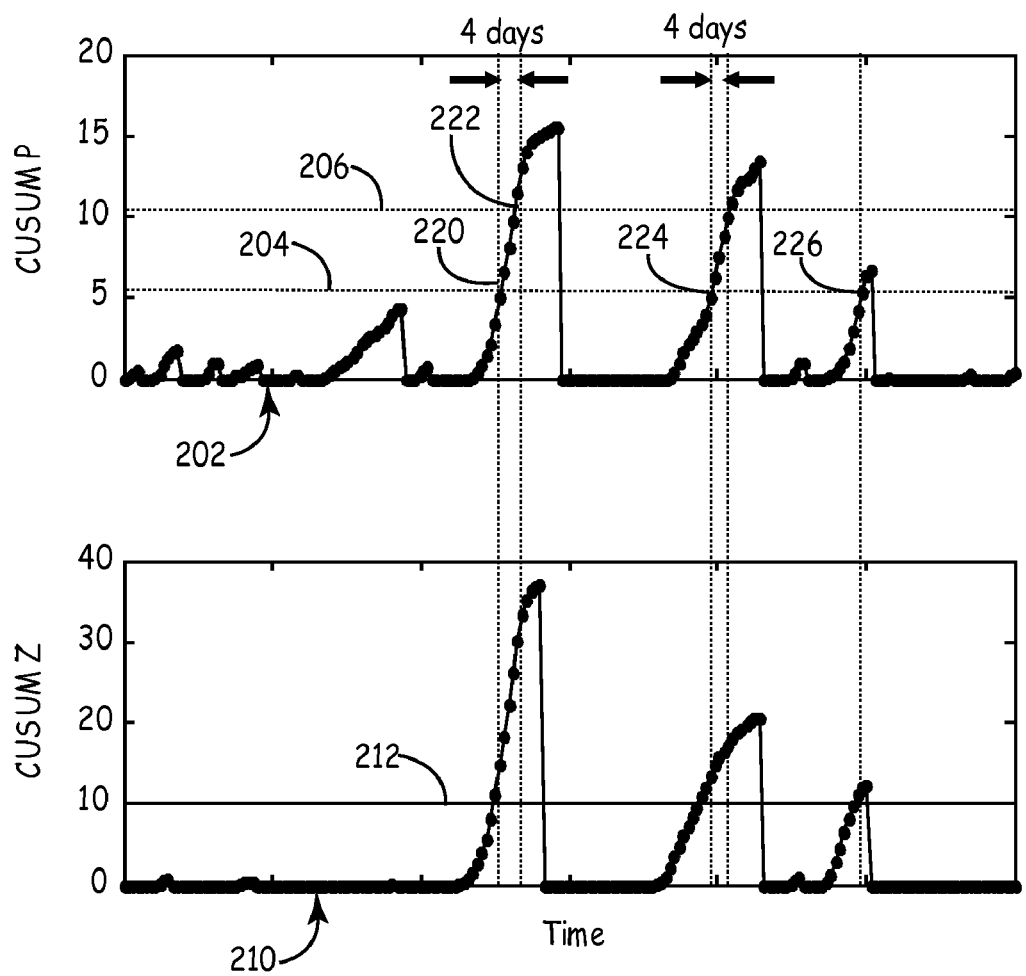
FIG. 3 is a diagram of two heart failure variables used for detecting heart failure decompensation.

FIG. 3 is a diagram of two heart failure variables used for detecting heart failure decompensation. Various embodiments for detecting decompensation include determining values of a pressure variable corresponding to right heart pressure signals obtained using a RV pressure sensor. In the example shown in FIG. 3, ePAD pressure is derived from the right ventricular pressure signal. Generally, ePAD pressure is determined as the RV pressure occurring at an inflection point in the RV pressure waveform which corresponds to the time of pulmonary valve opening. The time of this inflection point can be found by finding the time of the peak of the first time derivative of the RV pressure signal. Methods for deriving ePAD pressure are generally described in U.S. Pat. No. 5,368,040 (Carney), incorporated herein by reference in its entirety. A cumulative sum (CUSUM P) of the differences between an ePAD pressure value and a measured baseline is determined as the monitored pressure variable 202. Increases in CUSUM P 202 indicate the presence of increasing pressure changes consistent with increased filling pressure since ePAD pressure is an estimate of left atrial pressure (when systolic pressure variables are used trends in afterload can be monitored). Additional details relating to computing a cumulative sum variable are described below with regard to an impedance variable and are applicable for computing a cumulative sum pressure variable as well.

At least two different threshold levels 204 and 206 are used for setting an adjustable decompensation detection threshold. The decompensation detection threshold is adjusted to one of the two threshold levels 204 and 206 at any given time based on a value of an impedance variable 210.

Impedance variable values 210 are determined as a cumulative sum of the difference between a baseline impedance and an intrathoracic impedance measurement. A cumulative sum of impedance values (CUSUM Z) 210 is thereby determined as an impedance-related heart failure variable. Decreasing intrathoracic impedance, indicated by increases in CUSUM Z 210, is consistent with increasing thoracic fluid and is thus useful in detecting cardiac decompensation.

CUSUM Z 210 may be computed as a summation of the differences between daily mean impedances and a baseline impedance. In some embodiments, hard limits, called "winsorization", can be placed on the differences before they are summed, to decrease the effects of outlier values of daily mean impedance. Other approaches to outlier limiting can also be used. A daily impedance measurement may be computed from periodic measurements taken over any predetermined interval of time each day, including all twenty-four hours of the day. A baseline impedance value is also computed as a mean value of periodic impedance measurements taken over a predetermined time interval. Either the daily mean or the baseline can be computed using a linear method (e.g., a running average) or a non-linear method (e.g., a running median or a counter) for estimating and tracking a central tendency of the intrathoracic impedance measurements collected over a defined time interval. CUSUM Z 210 is updated each time a new daily mean impedance is computed, but, in some embodiments, CUSUM Z 210 is updated conditionally depending on how the new daily mean impedance compares to the baseline.

The baseline itself may also be updated in different ways over time. For example, the baseline could be updated more quickly for daily mean impedances above the baseline than for daily mean impedances below the baseline. Alternatively, the baseline may not be updated at all or updated depending on the difference between the new daily mean impedance and the baseline. The CUSUM Z 210 can be automatically zeroed at any time under any number of pre-defined conditions, e.g. when a short-term average of the daily impedance values goes above the baseline. This increase in a short-term average of daily impedance values is an indication that thoracic fluid levels have decreased such that the thoracic fluid accumulation leading to an increasing CUSUM Z 210 has been resolved.

An adjustment threshold 212 is set for impedance variable 210. If the impedance variable value 210 exceeds the adjustment threshold 212, the adjustable decompensation detection threshold is adjusted to the lower pressure threshold level 204 for use in detecting decompensation. If the impedance variable value 210 is less than the adjustment threshold 212, the adjustable decompensation detection threshold is adjusted to the higher pressure threshold level 206 for use in detecting decompensation. In other words, the pressure threshold for detecting decompensation is set to level 204 or 206 based on the impedance variable value 210 relative to an adjustment threshold 212. When the impedance variable value 210 is relatively low, i.e., not indicative of increasing thoracic fluid, a higher pressure variable value 202 is required to detect heart failure decompensation. However, when the impedance variable value is relatively high, i.e. indicative of increasing thoracic fluid, a lower pressure variable value in combination with the increased impedance value support a detection of heart failure decompensation.

In FIG. 3, only one adjustment threshold level 212 is shown and two adjustable decompensation detection threshold levels 204 and 206 are shown. It is recognized that additional threshold levels may be defined for both the pressure variable and the impedance variable such that as the impedance value exceeds higher adjustment threshold levels, the decompensation detection threshold is inversely adjusted to lower levels. This adjustment may occur in a stepwise manner, i.e. step changes in the adjustable detection threshold are made in response to the impedance variable 210 crossing the adjustment threshold. Alternatively, continuous or semi-continuous adjustments in the decompensation detection threshold may be made in response to changes in the impedance variable values 210.

At 220, a decompensation detection is made based on the pressure variable 202 exceeding the decompensation detection threshold adjusted to level 204 in response to impedance variable 210 exceeding adjustment threshold 212. This detection at 220 is shown to occur four days earlier than a decompensation detection that would have occurred at 222 based on pressure variable 202 exceeding the higher pressure threshold level 206. As such, the combination of the two heart failure variables with inter-variable threshold dependency allows for earlier detection of heart failure decompensation.

Second and third detections 224 and 226 occur in a similar manner as variable 202 exceeds a detection threshold set at threshold level 204 in response to the impedance variable 210 exceeding adjustment threshold 212. Without the adjustment of the detection threshold to level 204 in response to the impedance 210 exceeding adjustment threshold 212, the third detection 226 would not have occurred since the pressure variable 202 never exceeds the second threshold level 206. In this case, no detection would have occurred when in fact a worsening condition may be present. The heart failure variable-dependent adjustment of the decompensation detection threshold potentially improves sensitivity and specificity of decompensation detection.

In the example of FIG. 3, the decompensation detection threshold is applied to the pressure variable 202 and is adjusted in response to the value of the impedance variable 210. The pressure variable 202 may be referred to as the primary variable for detecting decompensation. In alternative embodiments, impedance variable 210 may be used as the primary variable in which case the decompensation detection threshold is applied to the impedance variable 210 and is adjusted in response to changes in the value of pressure variable 202.

Pressure and impedance variables could be used individually or in combination for detecting a worsening heart failure condition based on independently defined thresholds. However, in such approaches, the variables may not be in agreement in terms of the variable trend or the timing of a detection. Once one variable reaches a threshold defined to provide a high confidence of correct positive decompensation detections, the decompensation detection may be delayed. Likewise, the time needed for multiple variables to reach independently-defined detection thresholds may delay decompensation detection. Defining variable interdependent thresholds allows two or more variables, each having moderate to good predictive power alone, to be used in combination to provide earlier, more sensitive and more specific detection of heart failure decompensation than when those same variables are used individually or in combination with independently defined thresholds.

FIGS. 4A, 4B and 4C are diagrams illustrating other methods for setting a decompensation detection threshold for use in detecting heart failure decompensation. As discussed above, additional threshold levels may be defined for a heart failure variable to provide multiple step-wise, semi-continuous or continuous adjustments to a decompensation detection threshold in response to comparisons between another heart failure variable and multiple adjustment threshold levels.

In FIG. 4A, a pressure variable (labeled "P") is the primary detection variable, and pressure values 252 are plotted over time. A decompensation detection threshold 250 is adjusted in a stepwise manner in response to an impedance variable 256 crossing any of adjustment threshold levels 258, 258', 258', 258", or collectively 258. The adjustment threshold levels 258 are fixed threshold levels used for determining when to adjust the decompensation detection threshold 250. The impedance variable 256 is seen to increase and, with each adjustment threshold level crossing, the decompensation detection threshold 250 is decreased. At 254, a decompensation detection is made based on the pressure variable 252 crossing the impedance-dependent decompensation detection threshold 250.

In FIG. 4B, the decompensation detection threshold 260 is shown to be "continuously" adjusted with changes in the impedance variable 266. With each newly measured impedance value, a new decompensation detection threshold 260 is computed. A detection 264 is made when the pressure variable 262 crosses the "continuously" adjusted, impedance-dependent detection threshold 260. As used herein, "continuously adjusted" is intended to indicate that each time a new value of the impedance variable is determined, the pressure threshold is updated. It is recognized, however, that this is a discrete process in that the adjustment occurs at the time points the impedance variable value is updated. The step-size that the pressure threshold is adjusted in response to a given change in the impedance variable value may be constant or variable.

In FIG. 4C, the decompensation detection threshold 270 is semi-continuously adjusted. The pressure threshold 270 starts at a highest level 280 and remains there until a first adjustment threshold level 278 is exceeded by the impedance variable 276. A "continuous" adjustment of the decompensation detection threshold 270, as described above, occurs with each new measurement of impedance variable 276 until the decompensation detection threshold 270 reaches a middle threshold level 282. The decompensation detection threshold 270 is no longer updated with each new measurement of the impedance variable but is held at the middle threshold level 282 until the impedance variable 276 exceeds a next higher adjustment threshold level 278'. The decompensation detection threshold 270 is again adjusted "continuously" with changes in impedance 276 until a lower threshold level 284 is reached. The decompensation detection threshold 270 remains at the lower threshold level 284 until the impedance variable 276 exceed a next higher adjustment threshold level 278''', after which the decompensation detection threshold 270 is again "continuously" adjusted and so on. In this example, a decompensation detection is made at 274 when the pressure variable 272 exceeds the semi-continuously adjusted decompensation detection threshold 270.

In summary, a heart failure variable-dependent threshold applied to a primary variable for detecting decompensation may be adjusted each time a secondary variable value is updated, only when the secondary variable value crosses an adjustment threshold, or a combination of both. The magnitude of the adjustment to the variable-dependent detection threshold may be a constant step size or a varying step size. The step size may additionally be dependent on the level of the primary or secondary variable value.

In FIGS. 3 and 4, the pressure variable has been described as the primary variable and the impedance variable has been described as the secondary variable used only in setting the decompensation detection threshold applied to the primary variable. This approach may be referred to as "one-way threshold interdependence" in that the impedance value affects the detection threshold applied to the pressure variable, but the pressure variable value does not affect a detection threshold applied to the impedance variable.

In alternative embodiments, two-way interdependence may be implemented in which the value of each variable affects an adjustable decompensation detection threshold applied to another variable. In this way, two or more variables may be used with their respective detection threshold crossings given approximately equal weight in detecting decompensation. Threshold limits and/or the frequency at which a detection threshold may be adjusted may be limited to prevent instability or erratic behavior of the variable-interdependent thresholds.

Figure 5A:
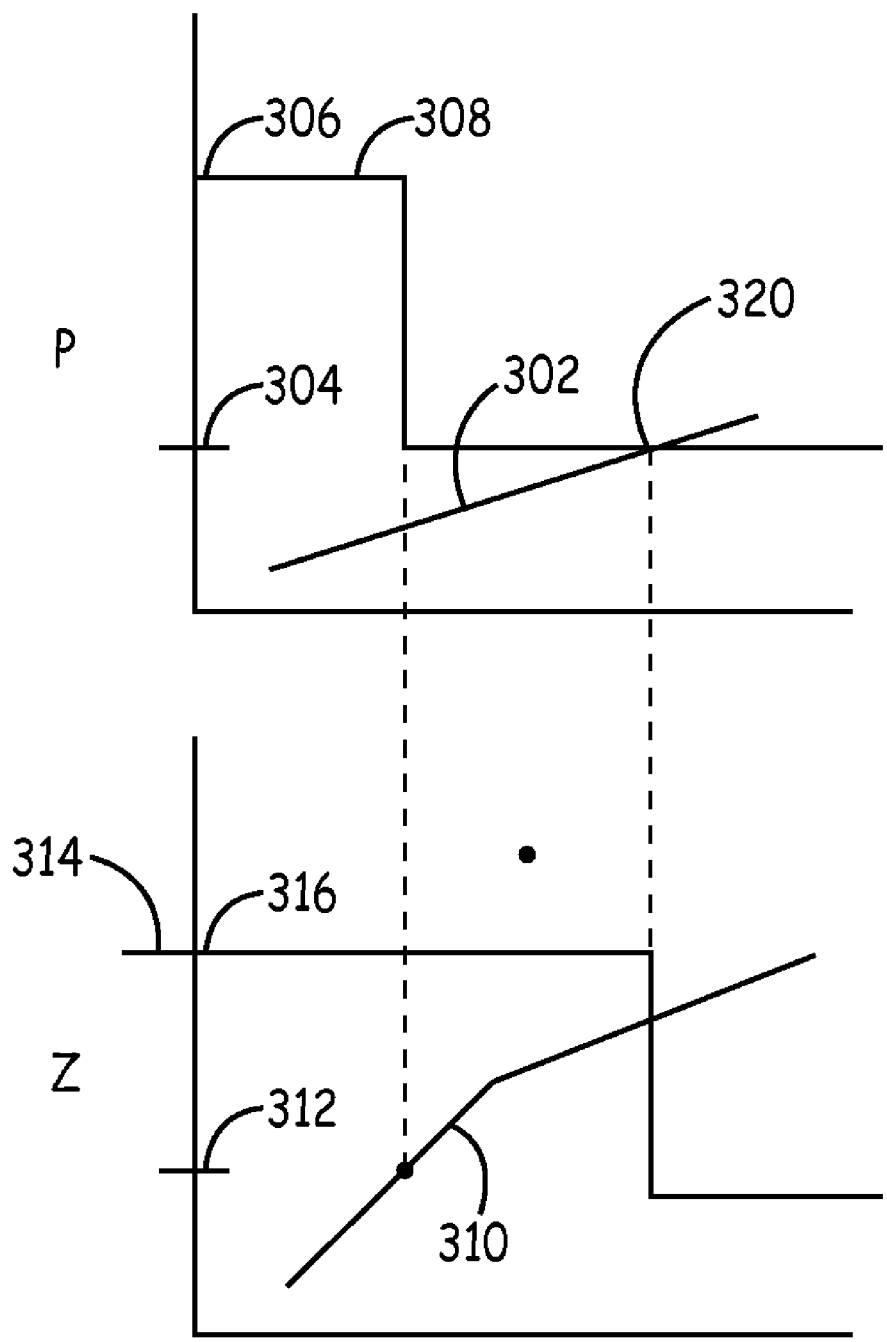
FIG. 5A is a diagram showing two-way threshold interdependence.

FIG. 5A is a diagram showing two-way decompensation detection threshold interdependence. For the sake of clarity, two variables, a pressure variable and an impedance variable, are shown in FIG. 5A. It is recognized that two-way interdependence may be implemented using additional variables. When three or more variables are used, the interdependence between any two variables may be two-way or one-way. Furthermore, a variable interdependent threshold may be adjusted as a function of any number of other heart failure variables being monitored.

In FIG. 5A a pressure variable 302 is monitored relative to two threshold levels 304 and 306. An impedance variable 310 is monitored relative to two threshold levels 312 and 314. The threshold levels 304, 306 and 312, 314 are fixed levels used to determine when to adjust a decompensation detection threshold applied to the other variable. The fixed threshold levels 304, 306 and 312, 314 are additionally used as the values which the decompensation detection thresholds are adjusted to in response to the value of the other variable.

Specifically, the decompensation detection threshold 308 applied to the pressure variable 302, referred to hereafter as the "pressure threshold" 308, is adjusted between levels 304 and 306 in response to comparing the impedance variable 310 to threshold level 312. Thus threshold level 312 serves as an adjustment threshold for determining when to adjust pressure threshold 308. When impedance variable 310 is below threshold level 312, the pressure threshold 308 used for detecting decompensation is adjusted up to pressure threshold level 306. When impedance variable 310 exceeds threshold level 312, the pressure threshold 308 is adjusted down to pressure threshold level 304.

Similarly, when the pressure variable 302 has a value below the lower pressure threshold level 304, decompensation detection threshold 316 applied to the impedance variable, referred to hereafter simply as the "impedance threshold" 316 is set at the higher threshold level 314. Thus threshold level 304 serves as an adjustment threshold for determining when to adjust impedance threshold 316. When the pressure variable 302 has a value exceeding the lower pressure threshold level 304, the impedance threshold 316 is adjusted down from impedance threshold level 314 to level 312.

In FIG. 5A, and in other embodiments described herein, the fixed threshold levels 304 and 312 serve two purposes. First, they are used to determine when the decompensation detection threshold for the other variable is adjusted. Second, they are used as one of the values to which an adjusted decompensation detection threshold is set to. In other words, pressure variable 302 will always be compared to fixed threshold level 304 for determining when to adjust the impedance threshold 316. Additionally, threshold level 304 is one of the two possible levels that pressure threshold 308, used for detecting decompensation, is adjusted to in response to the value of impendence variable 310.

Likewise, impedance variable 310 is always compared to fixed threshold level 312 for determining when to adjust the pressure threshold 308. Fixed threshold level 312 is additionally used as one of the levels impedance threshold 316 is adjusted to in response to the value of pressure variable 302.

It is recognized that a fixed threshold level defined for a given variable for determining when to adjust the decompensation detection threshold applied to another variable may be the same or different than decompensation detection threshold levels defined for the given variable. For example, a uniquely defined adjustment threshold level (not explicitly shown in FIG. 5A) that is different than fixed threshold levels 312 and 314, may be defined for comparison to impedance variable 310 for determining when pressure threshold 308 is adjusted. The threshold levels 312 and 314 would then be used exclusively as values to which impedance threshold 316 are adjusted to for detecting decompensation and would not be used for determining when to adjust pressure threshold 308.

A decompensation detection is made when either the pressure variable 302 has a value greater than threshold 308 set to the highest pressure threshold level 306 or the impedance variable 310 has a value greater than threshold 316 set to the highest impedance threshold level 314. A decompensation detection 320 can also be made when both the pressure variable 302 has a value greater than threshold 308 set to the lowest pressure threshold level 304 and the impedance variable 310 has a value greater than threshold 316 set to the lower impedance threshold level 312. Decompensation is not detected when both the pressure variable 302 and the impedance variable 310 are below their respective thresholds 308 and 316. While only two interdependent detection threshold levels are defined for each variable, it is recognized that any number of threshold levels may be defined for any of the illustrative embodiment described herein.

Figure 5B:
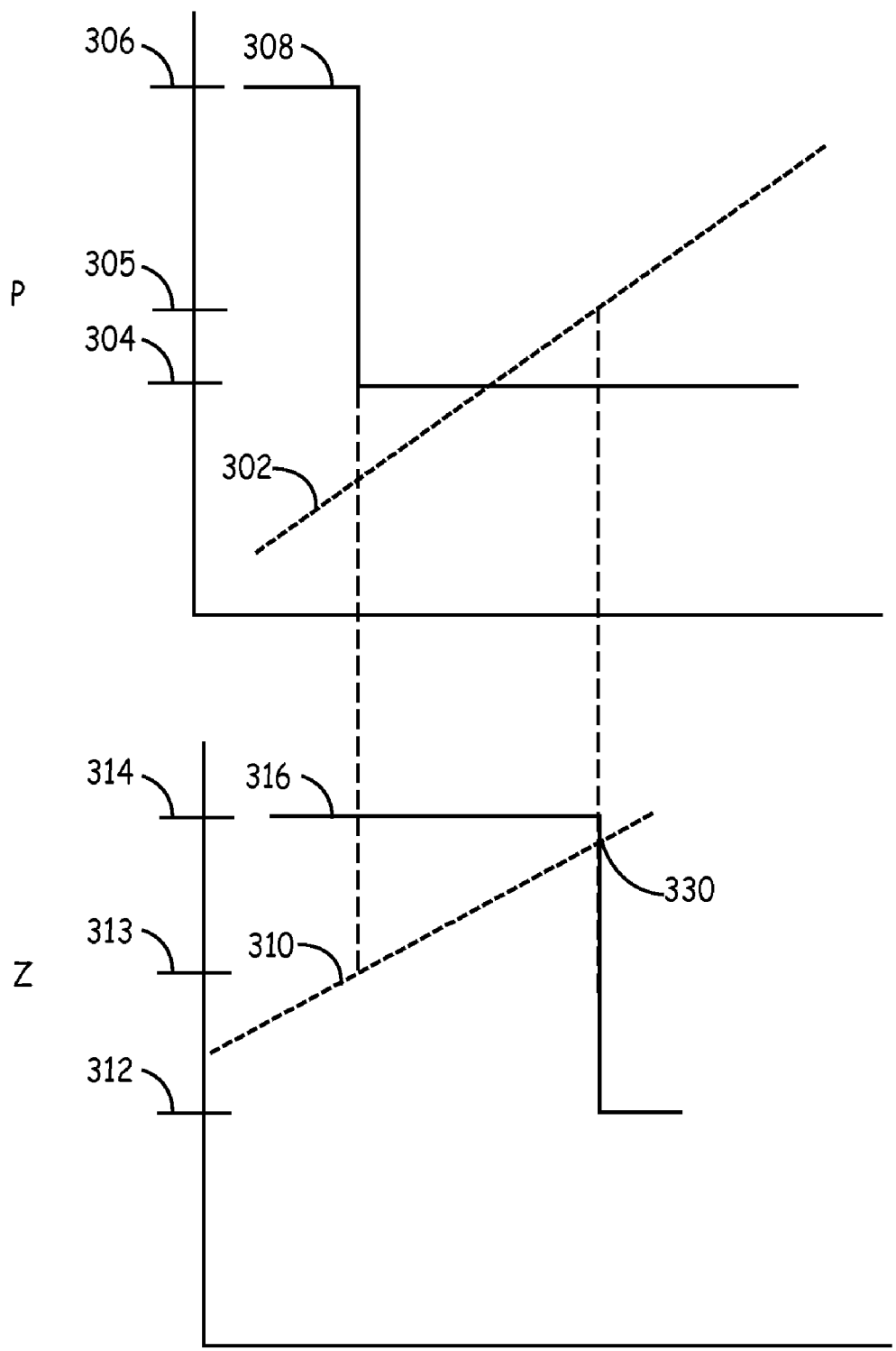
FIG. 5B is a diagram showing two-way threshold interdependence with separately defined adjustment thresholds and detection thresholds.

FIG. 5B is a diagram showing two-way threshold interdependence with separately defined adjustment thresholds and adjustable detection threshold levels. As shown in FIG. 5B, a pressure threshold 308 used for detecting decompensation is adjusted between fixed threshold levels 304 and 306 in response to the value of impedance variable 310. However, in this case, a fixed adjustment threshold 313 is defined separately from the impedance threshold levels 312 and 314 defined for adjustable impedance threshold 316. When impedance variable 310 crosses the adjustment threshold 313, pressure threshold 308 is adjusted from high threshold level 306 to low threshold level 304.

Similarly, an adjustment threshold 305 is applied to pressure variable 302 for determining when impedance threshold 316 should be adjusted. Adjustment threshold 305 is defined separately from the fixed threshold levels 304 and 306, between which pressure threshold 308 is adjusted for detecting decompensation. When pressure variable 302 crosses adjustment threshold 305, the impedance threshold 316 used for detecting decompensation is adjusted from level 314 down to level 312. At 330, both pressure variable 302 and impedance variable 310 have exceeded their respective adjustable thresholds 308 and 316, and a heart failure decompensation is detected.

Adjustment thresholds 305 and 313 are shown as values intermediate the pressure threshold levels 304 and 306 and the impedance threshold levels 312 and 314, respectively. In other embodiments, adjustment thresholds 305 and 313 may be greater or less than any given decompensation detection threshold level. For example, adjustment thresholds 305 and 313 may be less than detection threshold levels 304 and 312, respectively.

In summary, FIGS. 5A and 5B illustrate a two-way interdependence of decompensation detection thresholds for two different heart failure variables. The two-way interdependent detection thresholds are adjustable thresholds which are adjusted to two or more predefined threshold levels in response to the other variable crossing a fixed adjustment threshold. The fixed adjustment threshold may be equal to one of the adjustable decompensation detection threshold levels (as in the example of FIG. 5A) or different than the adjustable decompensation detection threshold levels (as in the example of FIG. 5B).

Figure 6:
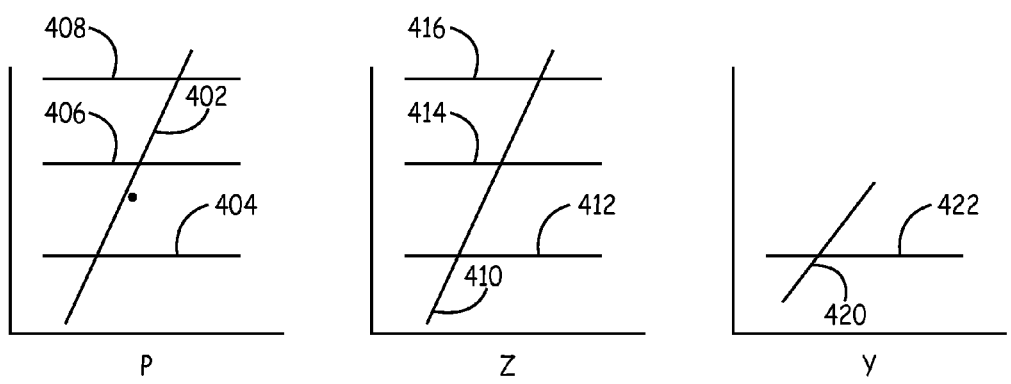
FIG. 6 is a schematic diagram of a variation of the detection method shown in FIG. 5A.

FIG. 6 is a schematic diagram of a variation of the detection method shown in FIG. 5A. In FIG. 6, the value of a pressure variable 402 is compared to a pressure threshold (not explicitly shown) for detecting decompensation which is set to one of three different threshold levels 404, 406 and 408 depending on the value of impedance variable 410. Likewise, impedance variable 410 is compared to an impedance variable threshold (not explicitly shown) for detecting decompensation which is set to one of three different threshold levels 412, 414 and 416 depending on the value of the pressure variable 402.

As generally described above in conjunction with FIG. 5A, the threshold levels 404, 406 and 412, 414 also serve as fixed adjustment threshold levels for determining when to adjust the decompensation detection thresholds for the other variable. For example, if the impedance variable 410 remains below its lowest threshold level 412, the pressure threshold is set to the highest threshold level 408 for detecting decompensation. If the pressure variable 402 remains below its lowest threshold level 404, the impedance threshold is set to the highest level 416. If either of the pressure variable 402 or the impedance variable 410 exceed their respective decompensation detection threshold set to the highest threshold level 408 or 416, respectively, decompensation is detected.

If the impedance variable 410 exceeds the middle threshold level 414, the pressure threshold for decompensation detection is set to middle threshold level 406. Likewise, if the pressure variable exceeds middle threshold level 406, an impedance threshold for detecting decompensation is set to middle threshold level 414. If both variables 402 and 410 cross their respective thresholds set to middle threshold levels 406 and 414, respectively, a decompensation detection is made. A detection is not made if only one variable 402 or 410 has crossed its threshold set to a middle threshold level 406 or 414, respectively.

If the adjustable thresholds for detecting decompensation for both the pressure variable 402 and impedance variable 410 remain set at their lowest levels 404 and 412, and both variables exceed their respective adjustable thresholds, a detection will only be made if a third confirming variable Y 420 has also crossed a threshold 422. In this scenario, both of the pressure and impedance variables crossing their respective detection thresholds set to the lowest threshold levels 404 and 412 is not enough evidence to support a detection of decompensation. A third heart failure related variable 420 is required to affirm the detection.

A pressure variable derived from a pressure sensor positioned in the right ventricle may relate to ePAD, RV systolic pressure, RV diastolic pressure or a mean RV pressure and may be determined as a running average, a slope of a mean value over time, or other statistical aspect of the RV pressure signal including a cumulative sum as described above. An impedance variable may likewise be derived as any of a number of statistical aspects of impedance measurements including, but not limited to, an average impedance determined over a predetermined interval of time, the rate of change of an impedance value over time, or a difference between an impedance measurement and a baseline measurement.

Additional variables that may be considered as third heart failure variable 420 include variables relating to heart rate, heart rate variability, activity level, respiration rate, tidal volume, arrhythmia episode frequency or burden (e.g., atrial fibrillation, ventricular fibrillation, or ventricular tachycardia). It is recognized that numerous heart failure variables and combinations of variables may be conceived for implementation in the inter-dependent detection threshold schemes used for detecting heart failure decompensation as described herein.

Figure 7:
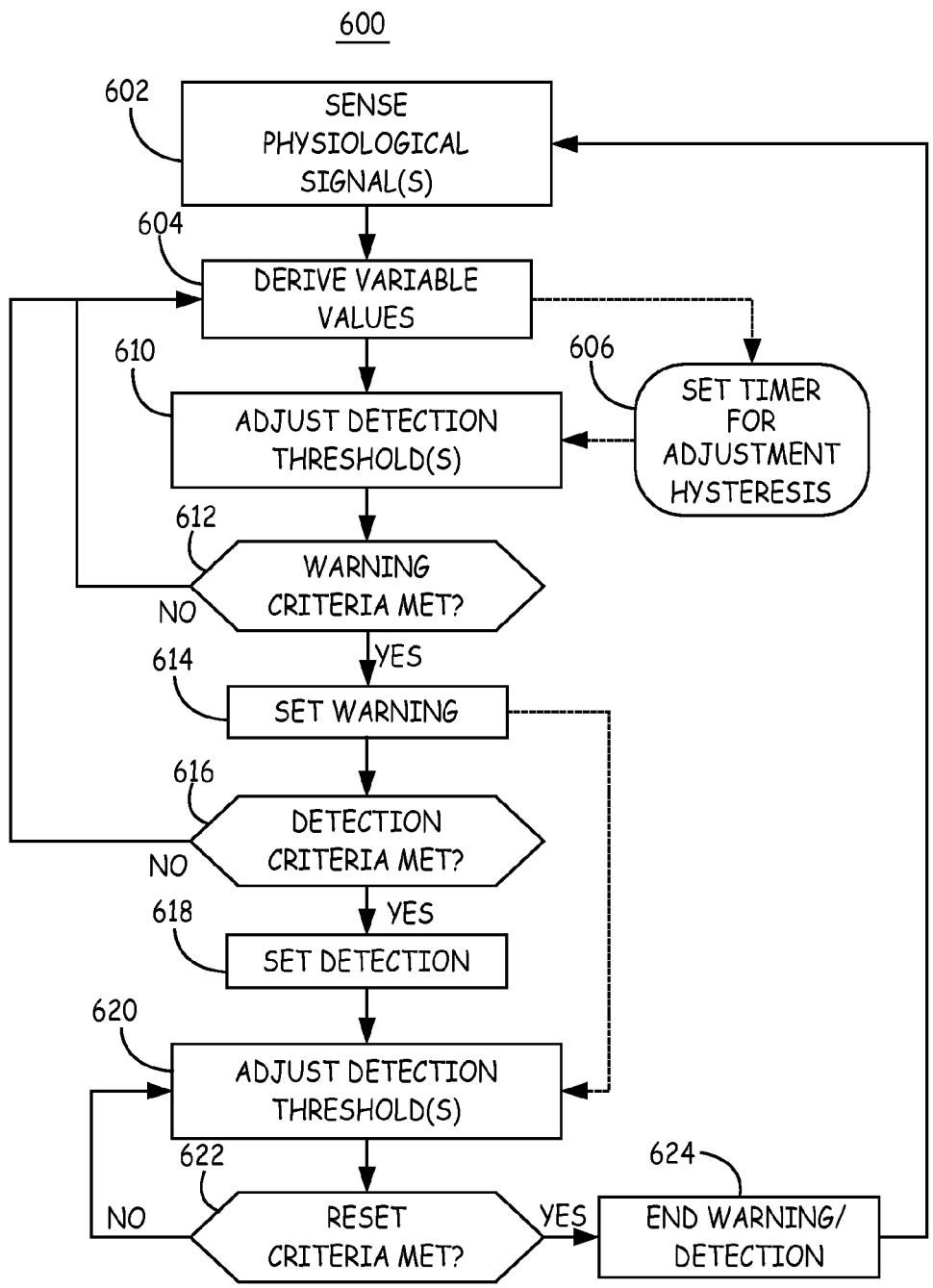
FIG. 7 is a flow chart of a method for detecting heart failure decompensation.

FIG. 7 is a flow chart of a method for detecting heart failure decompensation. Flow chart 600 is intended to illustrate the functional operation of the device, and should not be construed as reflective of a specific form of software or hardware necessary to practice the embodiments described herein. It is believed that the particular form of software will be determined primarily by the particular system architecture employed in the device and by the particular detection and therapy delivery methodologies employed by the device. Providing software to accomplish the described functionality in the context of any modern implantable device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 602 one or more physiological signals are sensed from which values for selected heart failure variables can be derived at block 604. As indicated above, RV pressure and transthoracic impedance signals are sensed in one embodiment from which values for ePAD pressure and thoracic impedance variables, respectively, can be derived.

The signal sensing at block 602, the frequency of deriving variable values at block 604, and the frequency of adjusting decompensation detection threshold(s) to variable-interdependent threshold level(s) may vary between embodiments. For example, signal sensing may occur on a continuous, semi-continuous, or periodic basis depending on the expected time variation of the monitored variables and the amount of data needed to derive variable values. Likewise, the variable values may be derived on a continuous, semi-continuous or periodic basis depending on how often an updated value is desired and the amount of data required for updating the variable value. The adjustable detection thresholds may be adjusted to different levels with each variable value update or on a less frequent basis. Generally, the more frequently the variable values and detection threshold levels are updated, the earlier heart failure decompensation can be detected, enabling earlier therapeutic or clinical intervention.

At block 610, a decompensation detection threshold for at least one variable is adjusted to a variable-dependent threshold level. As described above, the value of one heart failure variable may be used to set the detection threshold applied to another, primary detection variable in a one-way interdependence. Alternatively the values of both heart failure variables may be used set the decompensation detection thresholds applied to each other in a two-way interdependence. Any of the various methods described previously herein may be used in adjusting variable-interdependent decompensation detection thresholds at block 610.

The detection threshold adjustments at block 610 may optionally include a hysteresis effect as indicated by block 606. If a variable value determined at block 604 crosses an adjustment threshold that will normally cause adjustment of the detection threshold applied to another variable, a time delay may be required before adjustment of the detection threshold occurs. As long as the adjustment threshold crossing of the first variable value is maintained for a predetermined interval of time, the adjustment of the decompensation detection threshold applied to another variable will occur. However, if the adjustment threshold is crossed again by the first variable within the predetermined interval of time, a decompensation detection threshold will not be adjusted. Such hysteresis introduces stability to the algorithm by preventing frequent or erratic decompensation detection threshold adjustments caused, for example, by noise or artifacts in the sensed signals. This algorithm stability may avoid false detections or rapid switching between states of detecting and not detecting.

At block 612, derived variable value(s) are compared to the adjusted detection threshold(s) for determining if warning criteria are met. If warning criteria are met, a warning status is set at block 614. A warning state indicates heart failure decompensation is likely occurring. Setting the warning status may cause a patient or clinician alarm to be generated, cause the IMD to deliver or adjust a therapy, collect and store physiological data or adjust data acquisition, initiate data transmission to an external device, or execute other warning responses. The warning status may correspond to a change in variable values relative to adjusted detection thresholds that indicates worsening heart failure that warrants careful monitoring and possible clinical or therapeutic intervention.

At block 616, derived variable value(s) are compared to the adjusted detection threshold(s) for determining if decompensation detection criteria are met. A decompensation detection state may indicate with higher probability that heart failure decompensation is occurring than the warning state. For example, the value of one or all of the monitored variables may exceed a higher threshold level than the threshold levels required for setting the warning status. If the detection criteria are met, a detection state is set at block 618. A response to the detection state at block 618 may also include generating a patient and/or clinician alarm as well as adjusting patient therapy and/or data acquisition operations executed by the IMD.

After setting a warning status and/or a detection status, the detection thresholds are again adjusted according to comparisons between updated heart failure variable values and adjustment thresholds. A comparison between the heart failure variable value(s) and the adjusted detection threshold(s) at block 622 is performed to determine if reset criteria are met. Reset criteria define conditions which indicated the heart failure decompensation condition has been reversed, i.e. the heart failure variable values have returned to levels that do not indicate decompensation.

The threshold levels used at block 620 for adjusting the detection threshold for detecting a reset state may be the same or different than the threshold levels used for adjusting the detection threshold at block 610 for detecting the warning and detection states.

Alternatively, the threshold levels used for adjusting a detection threshold at block 620 after setting the warning or detection states may be the same as the threshold levels used for adjusting the detection threshold at block 610 but the criteria for detecting the reset state applied at block 622 may be different than a simple reversal of the warning or detection criteria applied at block 612. For example, in order to detect a decompensation state at block 618, both a pressure variable value and an impedance variable value may be required to exceed a detection threshold adjusted to a respective high threshold level. Instead of requiring both variables to fall below their respective detection thresholds in order to detect a reset state, only one or the other variable falling below its respective detection threshold may satisfy the reset criteria.

If the reset criteria are satisfied at block 622, the existing warning or detection state is ended at block 624. A response may be provided that includes a patient and/or clinician notification, a therapy response and/or a data acquisition response.

FIG. 8A is a truth table 400 that may be used as criteria for setting a warning or detection state, and FIG. 8B is a truth table 401 that may be used as criteria in ending a warning or detection state. In FIG. 8A, three states are shown, 0, 1 and 2, for each of a pressure variable 402 and an impedance variable 404. The three states correspond to two detection threshold levels for each variable. When a respective variable value is below a lowest threshold level, the variable is in the '0' state. When the variable value is greater than the lowest threshold level but less than the highest threshold level, the variable is in the '1' state, and when greater than the highest threshold level the variable is in the '2' state.

The truth tables 400 and 401 assume that the adjustment threshold for a given variable used for determining when the decompensation detection threshold applied to the other variable is adjusted is equal to the low threshold level for the given variable. As such, the pressure threshold will be adjusted from a high level to a low level when the impedance variable moves from a '0' state to a '1' state. The impedance threshold will be adjusted from a high level to a low level when the pressure variable 402 moves from a '0' state to a '1' state.

The "result" column 406 indicates the result of applying detection criteria to the variable values. The detection criteria include setting a detection threshold based on the 0, 1 or 2 state of the other variable. If both variables are in the '0' state, no event is detected 412. Both adjustable decompensation detection thresholds would remain at the highest threshold level for the given variable.

If one variable 402 or 404 is in the '0' state and the other is in the '1' state, no event is detected 414. The detection threshold for the variable in the '1' state remains at the highest threshold level because the other variable is still in the '0' state. The detection threshold for the variable in the '0' state is adjusted to the lower level due to the other variable being in the '1' state.

If both variables 402 and 404 move into the '1' state, the detection thresholds for both variable are adjusted to their respective lower threshold levels, and a detection state 416 is set as indicated in the result column 406. For any combination of '1' and '2' states (both variables in '1' state, both variables in '2' state, or one variable in '1' state and one variable in '2' state), the detection state 416 is set.

If either variable 402 and 404 is in the '0' state, the detection threshold for the other variable 402 or 404 is set to the highest threshold level. If the other variable exceeds the highest threshold level, i.e. reaches the '2' state, a warning state 418 is set.

In FIG. 8B, the result column 416 indicates the result of applying reset criteria to the variable values after a warning or detection state has been set. Table 400 effectively becomes inactive and truth table 401 becomes active upon entering a detection state. If either or both variables 402 and 404 return to a '0' state, the detection state is reset or ended 420. This occurs even when one variable 402 or 404 remains in a '2' state. As long as both variables 402 and 404 are in a '1' state or greater, the detection state remains valid 422.

Figure 9:
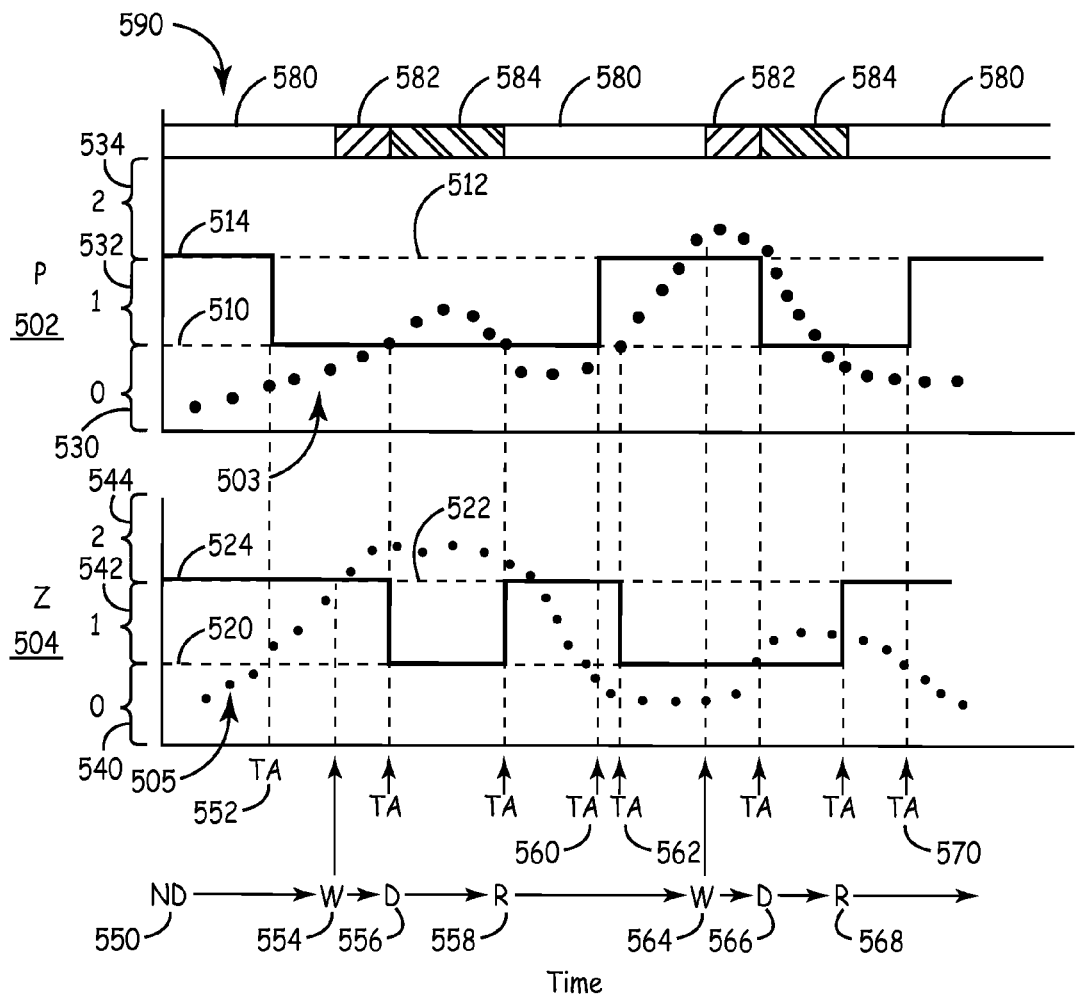
FIG. 9 is a timeline illustrating the adjustment of variable interdependent threshold levels and the decompensation detection state according to one embodiment.

FIG. 9 is a timeline illustrating the adjustment of heart failure variable-interdependent decompensation detection thresholds and the resulting decompensation detection state according to one embodiment. The events portrayed in FIG. 9 are illustrative in nature and not intended to necessarily represent actual clinical events. Values 503 for a pressure variable 502 may be computed as the cumulative sum of ePAD pressure changes from a baseline. Values 505 for an impedance variable 504 may be computed as the cumulative sum of short term average impedance changes from a baseline. The relationship between an adjustable pressure threshold 514 and an adjustable impedance threshold 522 in a two-way interdependence is illustrated.

Pressure threshold 514 used for detecting decompensation is shown to be adjusted between a low level 510 and a high level 512 in response to changes in the values 505 of the impedance variable 504. Likewise, the impedance threshold 524 used for detecting decompensation is adjusted between a low level 520 and a high level 522 in response to changes in the values 503 of the pressure variable 502. The low level 510 of adjustable pressure threshold 514 is used as a fixed adjustment threshold for determining when the impedance threshold 524 is adjusted. The low level 520 of adjustable impedance threshold 524 is likewise used as a fixed adjustment threshold for determining when the pressure threshold 514 is adjusted.

Initially, both decompensation detection thresholds 514 and 524 are set high as both the pressure and impedance variable values are in the '0' state 530 and 540 respectively, i.e., less than the adjustment thresholds set equal to the lowest threshold levels 510 and 520. A no event detection state 550 is set.

At 552, a threshold adjustment (TA) occurs. The impedance variable value 505 exceeds the lowest impedance threshold level 520 causing the pressure variable threshold 514 to be adjusted to the lowest pressure impedance threshold level 510. The pressure variable is in a '0' state and the impedance variable is in a '1' state 542 which corresponds to a no event detection state according to the example truth table of FIG. 8A. This is consistent with neither variable 503 nor 505 crossing its adjustable threshold 514 or 524. As such, the no detection state 550 persists even though pressure threshold 514 was adjusted.

The impedance threshold remains at the highest level 522 as long as the pressure variable remains below the lowest pressure threshold level 510, in the '0' state 530. At 554, the impedance variable value 505 exceeds the threshold 524 causing a warning state to be set. The pressure variable is still in the '0' state and the impedance variable is in the '2' state 544 corresponding to a warning state in the truth table of FIG. 8A.

At 556, the pressure variable value 503 exceeds the low threshold level 510 causing the impedance threshold 524 to be adjusted to its lower level 520. Now the pressure variable is in a '1' state 532 and the impedance variable is in a '2' state resulting a detection state being set at 556, in accordance with the truth table 400. Both variables 503 and 505 have exceeded their adjustable decompensation detection thresholds 514 and 524, respectively. The detection state remains until 558 at which time the pressure variable value 503 falls below adjusted threshold 514. The pressure variable is below low level 510, in a '0' state again, and the impedance variable is in a '2' state corresponding to a reset (R) or an end detection state being set at 558, according to truth table 401 of FIG. 8B.

At 558, 560 and 562, threshold adjustments occur in response to the changing variable values 503 and 505. At 558, the pressure variable value 503 falls below the lowest threshold level 510 causing the impedance threshold 524 to be adjusted to highest level 522. At 560, the impedance variable value 505 falls below the lowest threshold level 520 causing the pressure threshold 514 to be adjusted to the highest level 512.

Shortly thereafter, the pressure variable value exceeds the low threshold level 510 thereby entering the '1' state 532, causing the impedance threshold adjustment at 562. The pressure variable is in a '1' state and the impedance variable is in a '0' state such that the end detection state remains until the pressure variable value 503 exceeds the threshold 514 at 564. The pressure variable is now in a '2' state 534, and the impedance variable is in a '0' state resulting again in a warning state being set at 564 according to truth table 400.

At 566 a threshold adjustment occurs due to the impedance variable value 505 going above the lowest threshold level 520. The warning state is switched to a detection state since the pressure variable value 503 now exceeds the adjusted pressure threshold 514. The pressure variable has a '1' state and the impedance variable has a '1' state at 566 corresponding to a detection state in truth table 400.

The impedance variable threshold 524 is adjusted back up to the highest threshold level 522 at 568 due to the pressure variable value falling below the lowest pressure threshold level 510. Since both variables are less than their respective adjustable thresholds 514 and 524, the detection state is ended at 568. The pressure variable is in a '0' state and the impedance variable is in a '1' state corresponding to a reset event in truth table 401. At 570, another adjustment of the pressure threshold 514 occurs as the impedance variable value falls below the lowest threshold level 520.

As can be seen in the detection state timeline 590 shown along the top of FIG. 9, during no detection states 580, both variables 502 and 504 are below their respective two-way interdependent adjustable thresholds 514 and 524. During warning states 582, one variable 502 or 504 exceeds its adjusted threshold 514 or 524 and the other variable is below its adjusted threshold 514 or 524. During detection states 584, both variables 502 and 504 exceed their respective adjusted variable dependent thresholds 514 and 524. Thus, not only is there a threshold requirement applied to each variable 502 and 504 for detecting decompensation, that threshold requirement is adjustable and dependent on an updated value of the other variable.

Thus, methods and associated apparatus for detecting a cardiac condition using interdependent variable thresholds have been presented in the foregoing description with reference to specific embodiments. It is appreciated that various modifications to the referenced embodiments may be made without departing from the scope of the invention as set forth in the following claims.

The invention claimed is:

1. A method of detecting a heart failure condition in an implantable medical device system, comprising:
sensing at least one physiological signal;
enabling a processor to receive the at least one signal, determine a value of a first heart failure variable using the at least one physiological signal
and determine a value of a second heart failure variable using the at least one physiological signal; and
implementing a control unit to set a second threshold for the second heart failure variable to an initial threshold level, adjust a first threshold for the first heart failure variable in response to the value of the second heart failure variable value crossing the second threshold
compare the value of the first heart failure variable to the first threshold and
detect the heart failure condition in response to the comparison.

2. The method of claim 1 wherein adjusting the first threshold comprises adjusting the first threshold in response to a change in the second variable value.

3. The method of claim 1 further comprising adjusting the second threshold in response to the value of the first variable.

4. The method of claim 3 further comprising setting the first threshold to a first threshold level in response to the second variable value exceeding the initial threshold level and setting the first threshold to a second threshold level greater than the first threshold level in response to the second variable being less than the initial threshold level.

5. The method of claim 1 wherein adjusting the first threshold further includes verifying the value of the second variable does not cross the second threshold again for a predetermined period of time.

6. The method of claim 1 wherein detecting the heart failure condition further comprises comparing the value for the second variable to the second threshold.

7. The method of claim 1 further comprising:
determining a next value of the first variable and a next value of the second variable;
adjusting the first threshold in response to the next value of the second variable;
comparing the next value of the first variable to the adjusted first threshold; and
detecting the heart failure condition is no longer present in response to the comparison of the next value of the first variable to the adjusted first threshold.

8. The method of claim 1 wherein the at least one sensed signal comprises a right ventricular pressure signal.

9. The method of claim 8 wherein the at least one sensed signal further comprises a transthoracic impedance signal.

10. The method of claim 9 wherein the first variable corresponds to a pressure variable derived from the right ventricular pressure signal, and the second variable corresponds to a thoracic impedance variable derived from the transthoracic impedance signal.

11. A medical device for detecting a heart failure condition, comprising;
at least one sensor sensing at least one physiological signal;
a processor determining a value of a first heart failure variable and a value of a second heart failure variable using the at least one physiological signal; and
a control unit adjusting a first threshold for the first heart failure variable in response to the value of the second heart failure variable, comparing the value of the first heart failure variable to the first threshold, and detecting the heart failure condition in response to the comparison, the control unit configured to set a second threshold for the second variable to an initial threshold level and adjust the first threshold in response to the second variable value crossing the second threshold.

12. The device of claim 11 wherein the control unit adjusts the first threshold in response to a change in the second variable value.

13. The device of claim 11 wherein the control unit adjusts the second threshold in response to the value of the first variable.

14. The device of claim 13 wherein the control unit adjusts the first threshold to a first level in response to the second variable value exceeding the initial threshold level and sets the first threshold to a second level greater than the first level in response to the second variable being less than the initial threshold level.

15. The device of claim 11 wherein the control unit adjusts the first threshold further after verifying the value of the second variable does not cross the second threshold again for a predetermined period of time.

16. The device of claim 11 wherein the control unit compares the value for the second variable to the second threshold and detects the heart failure condition in response to the comparison of the second variable.

17. The device of claim 11 wherein the at least one sensor comprises a right ventricular pressure sensor.

18. The device of claim 17 wherein the at least one sensor further comprises a transthoracic impedance sensor.

19. The device of claim 18 wherein the processor determines a value of a pressure variable derived from the right ventricular pressure sensor signal, and a value of a thoracic impedance variable from the transthoracic impedance sensor signal.

20. A medical device for detecting a heart failure condition, comprising;
at least one sensor sensing at least one physiological signal;
a processor determining a value of a first heart failure variable and a value of a second heart failure variable using the at least one physiological signal; and
a control unit adjusting a first threshold for the first heart failure variable in response to the value of the second heart failure variable, comparing the value of the first heart failure variable to the first threshold, and detecting the heart failure condition in response to the comparison, wherein the processor determines a next value of the first variable and a next value of the second variable; and the control unit adjusts the first threshold in response to the next value of the second variable, compares the next value of the first variable to the adjusted first threshold, and detects the heart failure condition is no longer present in response to the comparison of the next value of the first variable to the adjusted first threshold.

21. A non-transitory computer readable medium storing a set of instructions which when implemented in a system cause the system to:

sense at least one physiological signal;

determine a value of a first heart failure variable using the at least one physiological signal;

determine a value of a second heart failure variable using the at least one physiological signal;

set a second threshold for the second variable to an initial threshold level;

adjust a first threshold for the first heart failure variable in response to the value of the second heart failure variable crossing the second threshold;

compare the value of the first heart failure variable to the first threshold; and detect a heart failure condition in response to the comparison.

* * * * *